United States Patent [19]

Breikss

[11] Patent Number: 5,523,453
[45] Date of Patent: Jun. 4, 1996

[54] PROCESS FOR HYDROCYANATION

[75] Inventor: Anne I. Breikss, Hockessin, Del.

[73] Assignee: E. I. Du Pont de Nemours and Company, Wilmington, Del.

[21] Appl. No.: 408,250

[22] Filed: Mar. 22, 1995

[51] Int. Cl.$^6$ .................................................. C07C 253/10
[52] U.S. Cl. .................................................. 558/338
[58] Field of Search ........................................ 558/338

[56] References Cited

U.S. PATENT DOCUMENTS

| | | | |
|---|---|---|---|
| 3,496,215 | 2/1970 | Drinkard et al. | 558/338 |
| 3,496,217 | 2/1970 | Drinkard, Jr. et al. | 558/338 |
| 3,496,218 | 2/1970 | Drinkard, Jr. et al. | 558/338 |
| 3,558,688 | 1/1971 | Drinkard, Jr. | 558/338 |
| 3,631,191 | 12/1971 | Kane et al. | 455/338 X |
| 3,655,723 | 4/1972 | Drinkard, Jr. | 558/338 |
| 3,766,237 | 10/1973 | Chia et al. | 558/338 |
| 3,846,461 | 11/1974 | Shook, Jr. | 558/338 X |
| 3,847,959 | 11/1974 | Shook, Jr. et al. | 558/338 X |
| 3,903,120 | 9/1975 | Shook, Jr. et al. | 558/338 X |
| 4,774,353 | 9/1988 | Hall et al. | 558/338 X |
| 4,874,884 | 10/1989 | McKinney et al. | 558/338 |
| 5,175,335 | 12/1992 | Casalnuovo et al. | 558/338 |

FOREIGN PATENT DOCUMENTS

WO93/03839  3/1993  WIPO .

OTHER PUBLICATIONS

Baker, et al.; J. Chem. Soc., Chem. Commun., (1991), pp. 1292–1293.
Baker, et al.; J. Chem. Soc., Chem. Commun., (1991), pp. 803–804.
Tolman, et al.; Advances in Catalysis, vol. 33, (1985), pp. 1–46.

*Primary Examiner*—Joseph Paul Brust

[57] ABSTRACT

A process for hydrocyanation of certain ethylenically unsaturated compounds which uses a catalyst composition comprising certain bidentate phosphorous compounds and zero-valent nickel in the presence of a Lewis Acid promoter.

5 Claims, No Drawings

PROCESS FOR HYDROCYANATION

FIELD OF THE INVENTION

This invention relates to a process for the hydrocyanation of certain monoethylenically unsaturated compounds, which uses zero-valent nickel and a bidentate phosphorous compound in the presence of a Lewis Acid promoter.

BACKGROUND OF THE INVENTION

Hydrocyanation catalyst systems, particularly pertaining to the hydrocyanation of olefins, are well known in the art. For example, systems useful for the hydrocyanation of butadiene to form pentenenitrile (PN) and in subsequent hydrocyanation of pentenenitrile (PN) to form adiponitrile (ADN), are known in the commercially important nylon synthesis field. The hydrocyanation of olefins using transition metal complexes with monodentate phosphite ligand is well documented in the prior art. See for example; U.S. Pat. Nos. 3,496,215, 3,631,191, 3,655,723, and 3,766,237, and Tolman, C. A.; McKinney, R. J.; Seidel, W. C.; Druliner, J. D.; and Stevens, W. R.; Advances in Catalysis, 33, 1, 1985. The hydrocyanation of activated olefins, such as with conjugated olefins (e.g., butadiene and styrene) and strained olefins (e.g., norbornene), proceeds without the use of a Lewis Acid promoter, while hydrocyanation of unactivated olefins, such as 1-octene and 3-pentenenitrile, requires the use of a Lewis Acid promoter. Teachings regarding the use of a promoter in the hydrocyanation reaction appear, for example, in U.S. Pat. No. 3,496,217. This patent discloses an improvement in hydrocyanation using a promoter selected from a large number of metal cation compounds with a variety of anions as catalyst promoters. U.S. Pat. No. 3,496,218 discloses a nickel hydrocyanation catalyst promoted with various boron-containing compounds, including triphenylboron and alkali metal borohydrides. U.S. Pat. No. 4,774,353 discloses a process for the preparation of dinitriles, including ADN, from unsaturated nitriles, including PN, in the presence of a zero-valent nickel catalyst and a triorganotin catalyst promoter. U.S. Pat. No. 4,874,884 discloses a process for producing ADN by the zero-valent nickel catalyzed hydrocyanation of pentenenitriles in the presence of a synergistic combination of promoters selected in accordance with the reaction kinetics of the ADN synthesis.

Bidentate phosphite ligands are useful ligands in the hydrocyanation of activated olefins. See, for example: Baker, M. J., and Pringle, P. G.; J. Chem. Soc., Chem. Commun., 1292, 1991; Baker, M. J.; Harrison, K. N.; Orpen, A. G.; Pringle, P. G.; and Shaw, G.; J. Chem. Soc.; Chem. Commun., 803, 1991, Union Carbide, WO 93,03839.

U.S. Pat. No. 5,175,335 to Casalnuovo et al. discloses the use of chiral, nonracemic, bidentate phosphinite ligands for the enantioselective hydrocyanation of aromatic vinyl compounds. The nickel-catalyzed hydrocyanation of these substrates occurs in a predominantly Markownikoff fashion. At Column 19, the '335 Patent shows Compound "F," a bidentate diphosphinite and shows its use in the hydrocyanation of 2-vinylnaphthalene.

SUMMARY OF THE INVENTION

The present invention provides a process for hydrocyanation, comprising reacting a nonconjugated, acyclic, aliphatic, monoethylenically unsaturated compound or 2-pentenenitrile or an alkyl-2-pentenoate with a source of HCN in the presence of a Lewis Acid promoter catalyst composition formed by a zero-valent nickel compound and a bidentate phosphorus compound or a mixture of bidentate phosphorous compounds selected from the group consisting of compounds having the formulae:

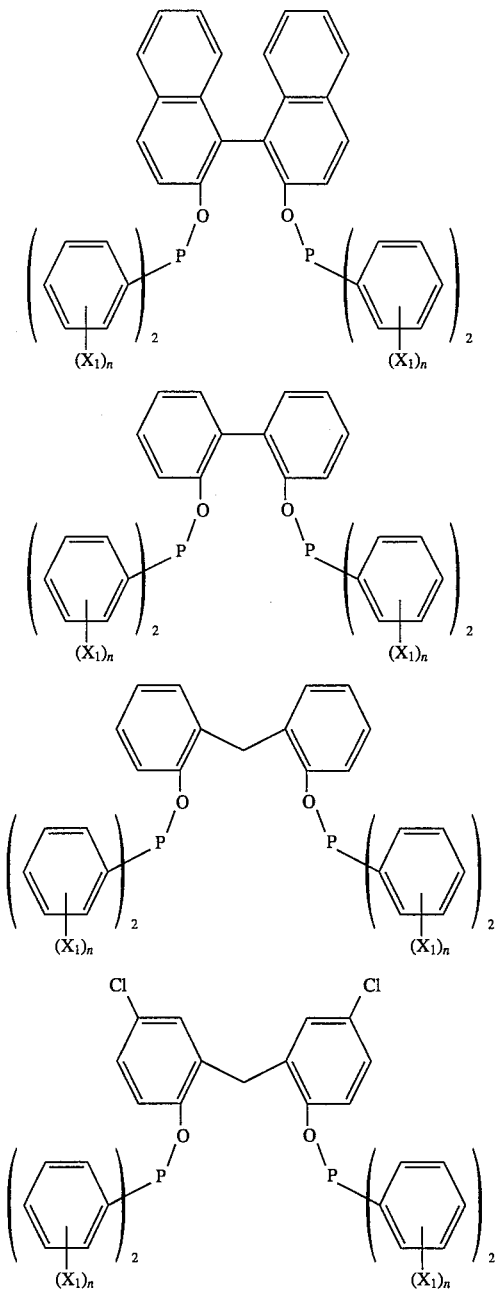

3
-continued
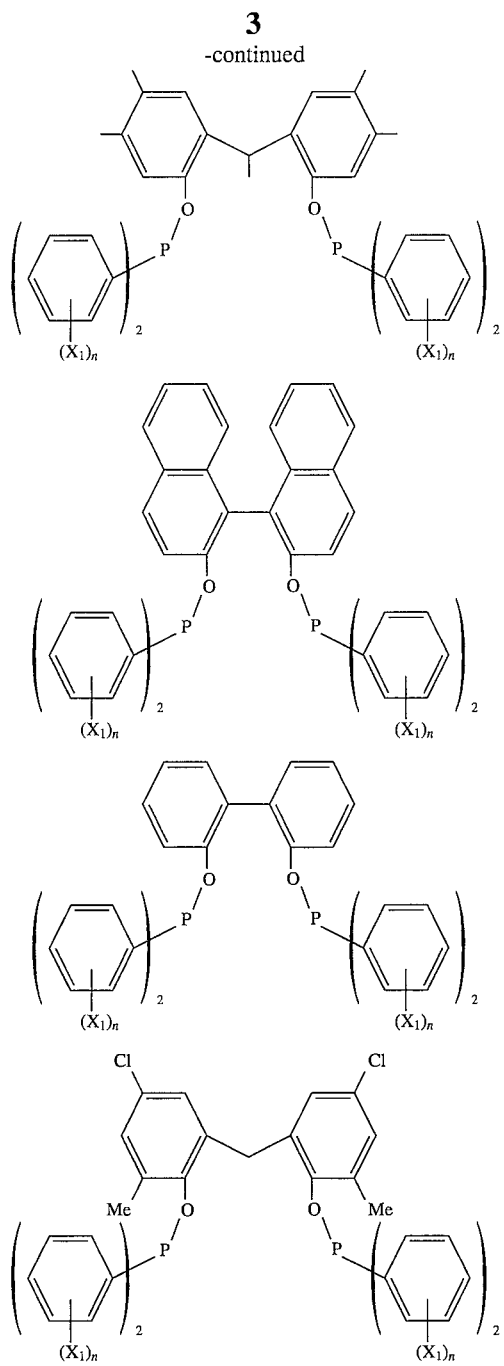
4
-continued
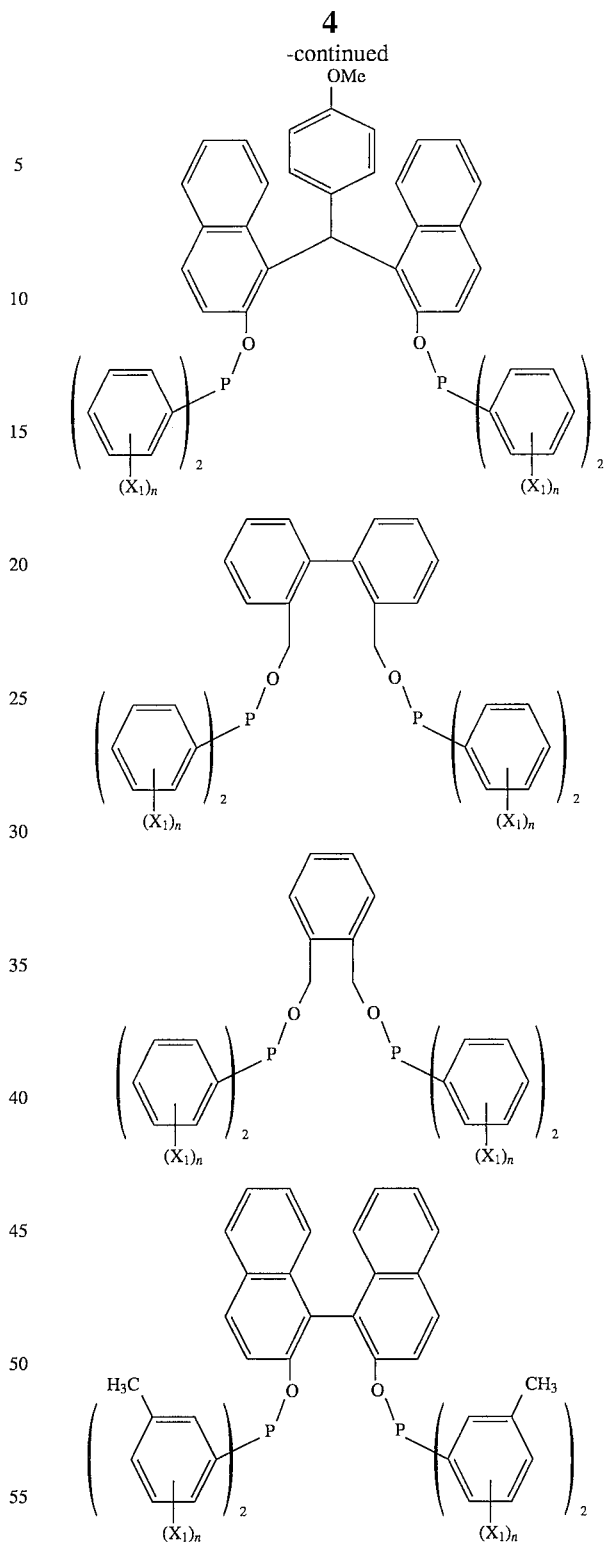

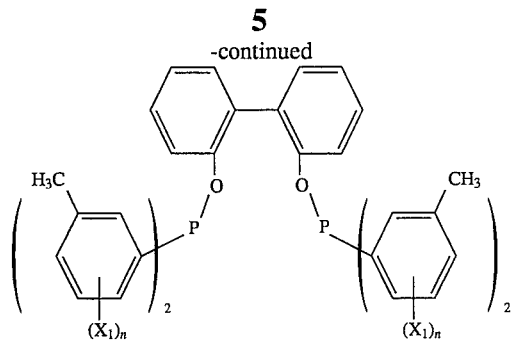
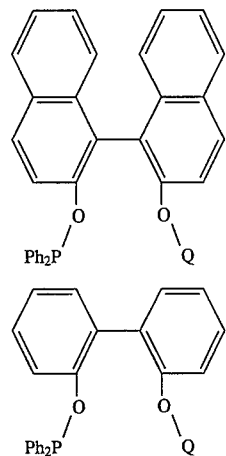
where $X_1$ is meta —Cl, para —Cl, meta —CF$_3$, para —CF$_3$, meta —P, para —F, meta —CN, para —CN, meta —CH$_3$ or para —CH$_3$; $X_2$ is methyl or alkoxy having 1 to 3 carbon atoms; n is zero, 1 or 2; Q is
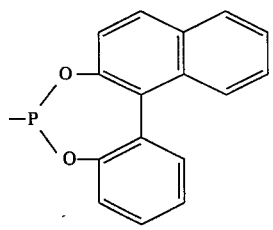
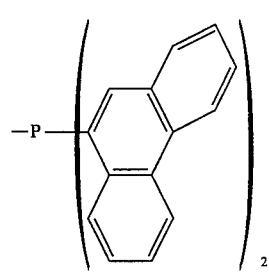
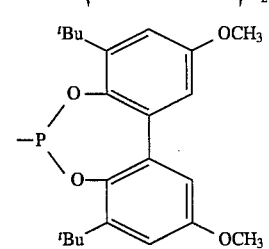
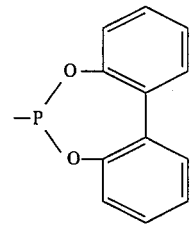
The addition of HCN to the double bond is primarily in the anti-Markownikoff manner.
The preferred bidentate phosphorus compounds have the formulae:
Formula 1
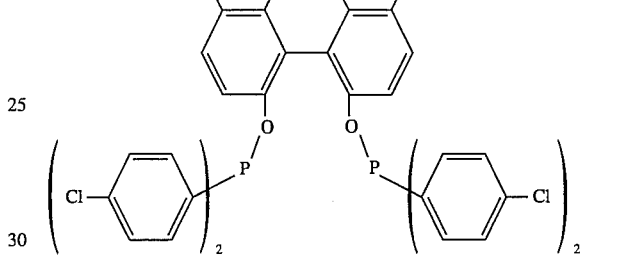
Formula 2
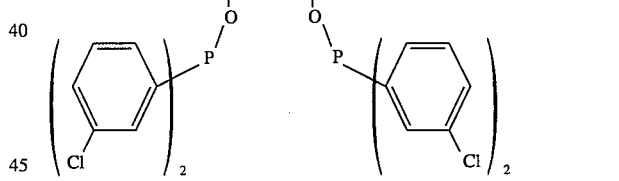
Formula 3
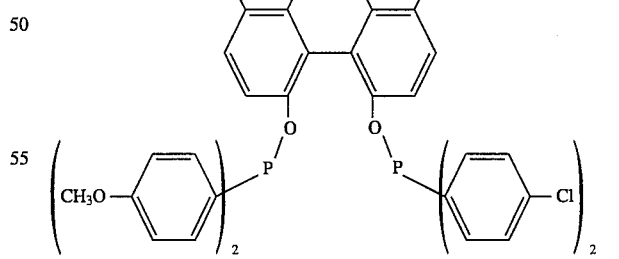

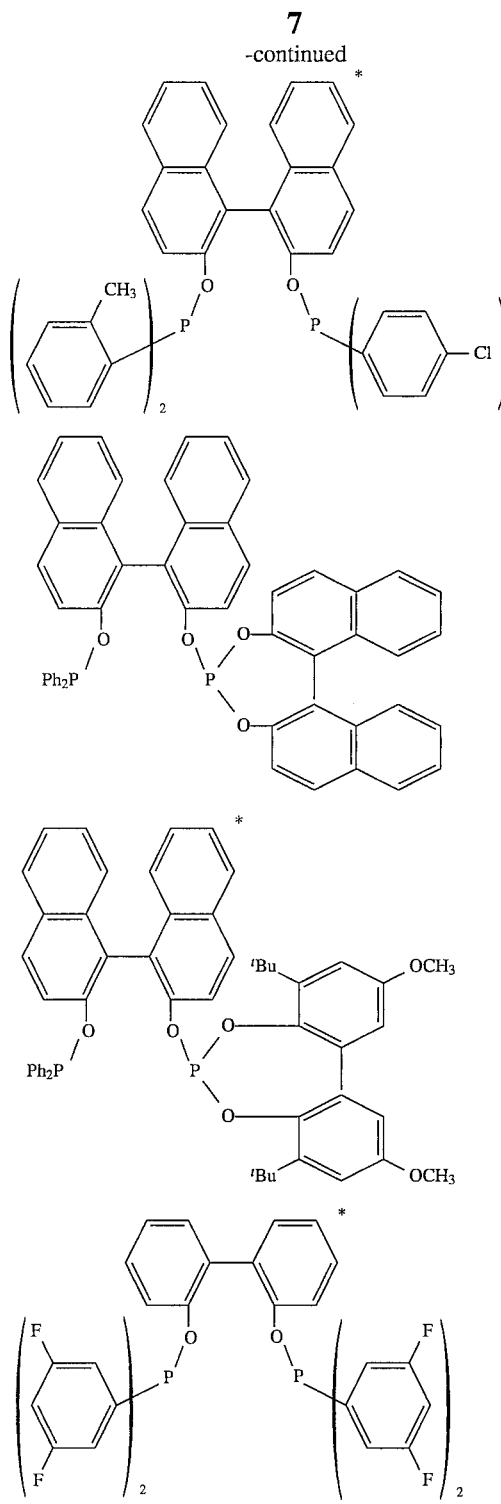
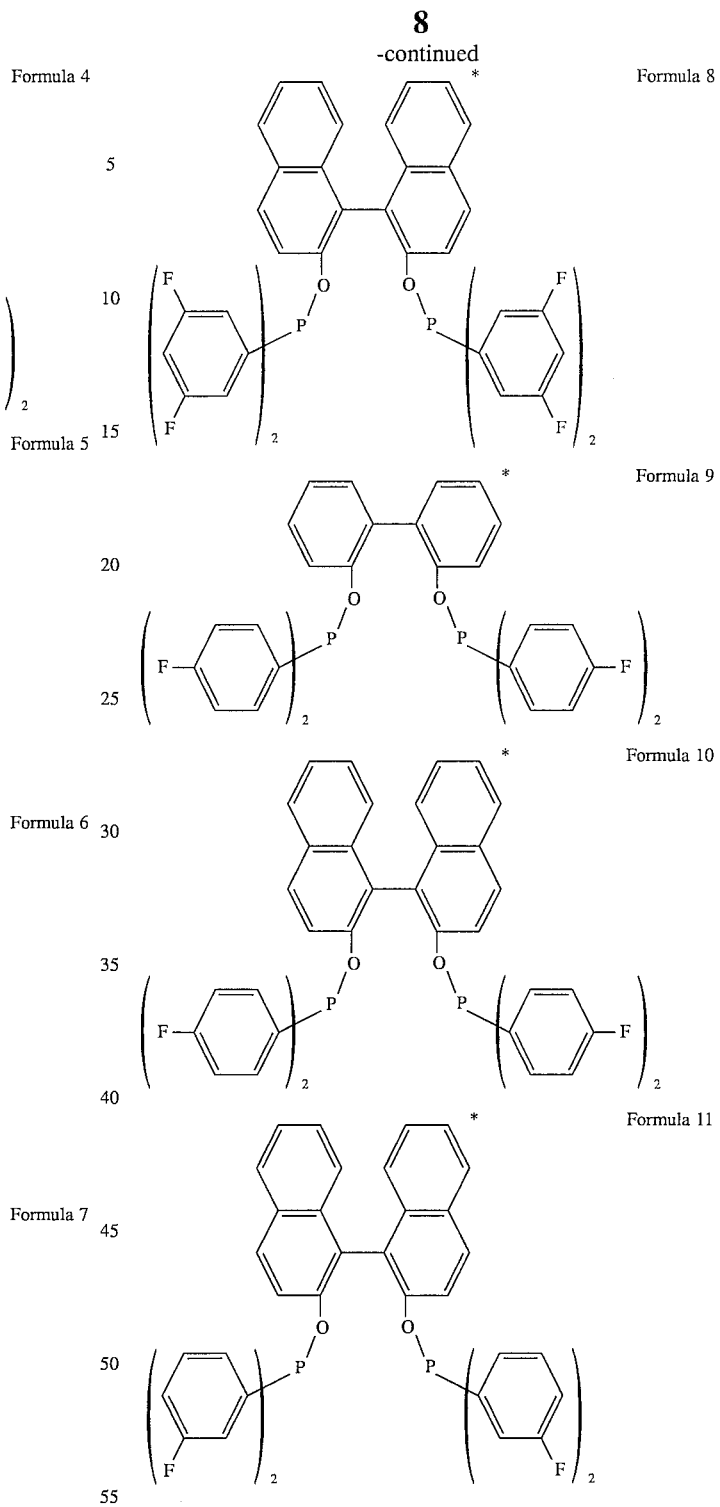

Formula 12
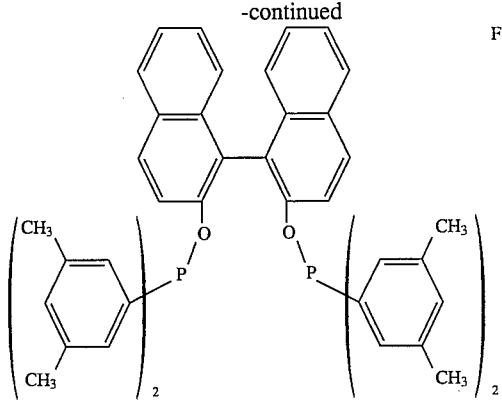
Formula 13
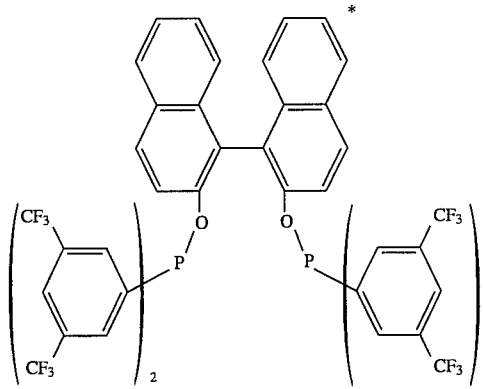
Formula 14
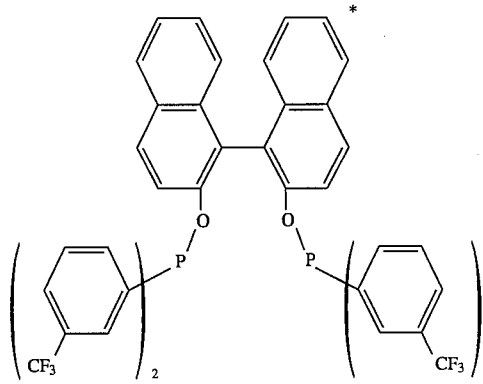
Formula 15
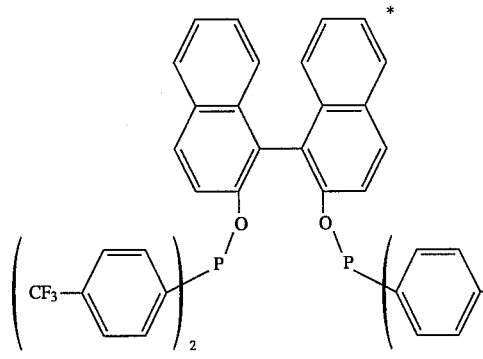
Formula 16
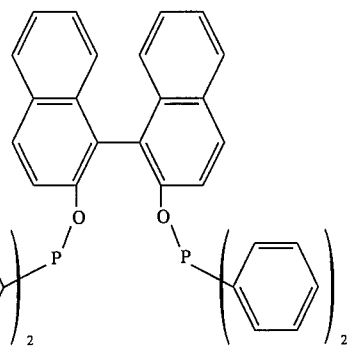
Formula 17
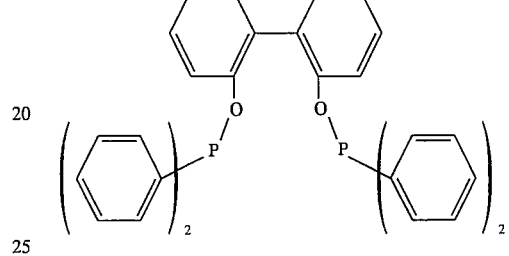
Formula 18
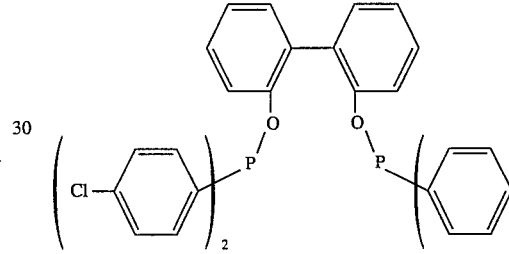
Formula 19
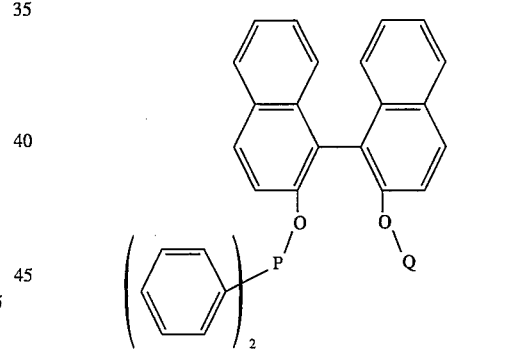
Formula 20
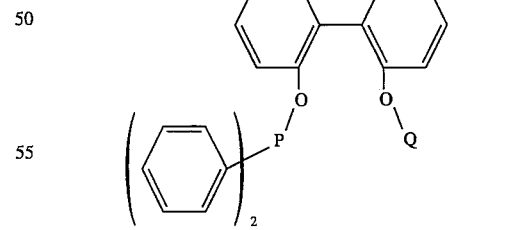
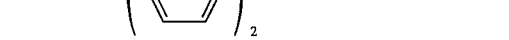

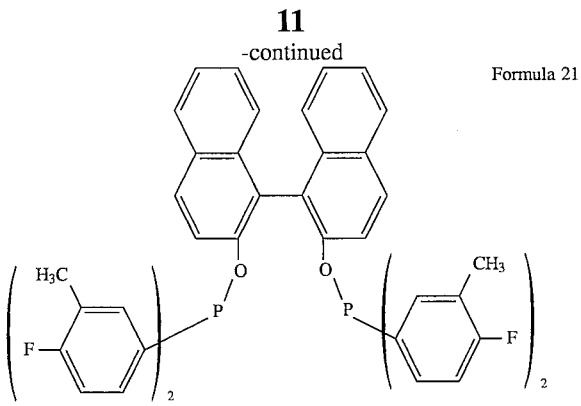

Formula 21 where Q is defined as previously. The most preferred compounds are shown above and marked with an asterisk (*).

DETAILED DESCRIPTION

The zero-valent nickel can be prepared or generated according to techniques well known in the art (U.S. Pat. No. 3,496,217; 3,631,191; 3,846,461; 3,847,959; and 3,903,120, which are incorporated by reference). Zero-valent nickel compounds that contain ligands, which can be displaced by the organophosphorus ligand, are a preferred source of zero-valent nickel. Two such preferred zero-valent nickel compounds are $Ni(COD)_2$ (COD is 1,5-cyclooctadiene) and $(oTTP)_2Ni(C_2H_4)$ (oTTP is $P(O\text{-}o\text{-}C_6H_4CH_3)_3$) both of which are known in the art. Alternatively, divalent nickel compounds may be combined with a reducing agent, and are then able to serve as suitable sources of zero-valent nickel in the reaction. Suitable divalent nickel compounds include compounds of the formula $NiY_2$ where Y is halide, carboxylate, or acetylacetonate. Suitable reducing agents include metal borohydrides, metal aluminum hydrides, metal alkyls, Zn, Fe, Al, Na, or $H_2$. Elemental nickel, preferably nickel powder, when combined with a halogenated catalyst, as described in U.S. Pat. No. 3,903,120, is also a suitable source of zero-valent nickel.

The present hydrocyanation process may be carried out by charging a reactor with all of the reactants, or preferably, the reactor is charged with the catalyst components, the unsaturated organic compound, the promoter, and the solvent to be used, and the hydrogen cyanide is added slowly. HCN may be delivered as a liquid or as a vapor to the reaction. Another technique is to charge the reactor with the catalyst, promoter, and the solvent to be used, and feed both the unsaturated compound and the HCN slowly to the reaction mixture. The molar ratio of unsaturated compound to catalyst generally is varied from about 10:1 to 2000:1. The molar ratio of phosphorous compound to nickel is in the range of 0.5 to 1 to 20 to 1.

Preferably, the reaction medium is agitated, such as by stirring or shaking. The cyanated product can be recovered by conventional techniques, such as by distillation. The reaction may be run either batchwise or in a continuous manner.

The hydrocyanation reaction can be carried out with or without a solvent. The solvent should be liquid at the reaction temperature and pressure and inert towards the unsaturated compound and the catalyst. Generally, such solvents are hydrocarbons, such as benzene or xylene, or nitriles, such as acetonitrile or benzonitrile. In some cases, the unsaturated compound to be hydrocyanated may serve as the solvent.

The exact temperature which is preferred is dependent to a certain extent on the particular catalyst being used, the particular unsaturated compound being used, and the desired rate. Generally, temperatures of from −25° to 200° C. can be used, with from 0° to 150° C. being preferred.

Atmospheric pressure is satisfactory for carrying out the present invention and, hence, pressure of from about 0.05 to 10 atmospheres are preferred due to the obvious economic considerations, although pressures of from 0.05 to 100 atmospheres can be used if desired.

HCN may be added to the reaction as vapor or liquid, or in a system utilizing a cyanohydrin as carrier. See, for example, U.S. Pat. No. 3,655,723 which is incorporated herein by reference.

The process of this invention is carried out in the presence of one or more Lewis Acid promoters which affect both the activity and selectivity of the catalyst system. The ratio (molar basis) of Lewis Acid to nickel is usually about 1 to 16 to 50 to 1. Suitable promoters are described in U.S. Pat. Nos. 3,496,217; 3,496,218; and 4,774,353.

A suitable Lewis Acid may be selected from the group consisting of inorganic or organometallic compounds in which the cation is selected from scandium, titanium, vanadium, chromium, manganese, iron, cobalt, copper, zinc, boron, aluminum, yttrium, zirconium, niobium, molybdenum, cadmium, rhenium, and tin.

Such Lewis Acids include compounds selected from the group consisting of $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$ $(THF)_2$, $TiCl_4(THF)_2$, $TiCl_4$, $TiCl_3$, $ClTi(OiPr)_3$, $MnCl_2$, $ScCl_3$, $AlCl_3$, $(C_8H_{17})AlCl_2$, $(iso\text{-}C_4H_9)_2AlCl$, $(phenyl)_2AlCl$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $TaCl_5$, $B(C_6H_5)_3$, and $(C_6H_5)_3SnX$, where $X=CF_3SO_3$, $CH_3C_6H_4SO_3$, $CH_3(CH_2)_{11}C_6H_4SO_3$, or $(C_6H_5)_3BCN$.

Preferred Lewis Acid promoters are $ZnCl_2$, $MnCl_2$, $FeCl_2$, $AlCl_2(C_8H_{17})$, $B(C_6H_5)_3$, $Er(CF_3SO_3)_3$, and $(C_6H_5)_3SnX$, where $X=(C_6H_5)_3BCN$ or $CH_3(CH_2)_{11}C_6H_4SO_3$.

The symmetrical bidentate phosphorus compounds (diphosphinites) are prepared as follows. The diarylchlorophosphine is added to a toluene solution of the diol and triethylamine. The reaction mixture is allowed to stir at room temperature, then filtered to remove triethylamine hydrochloride. The product is isolated by removing the solvent under reduced pressure.

The unsymmetrical bidentate phosphorus compounds (diphosphinites) are prepared in a similar manner. The first diarylchlorophosphine (preferably the more sterically hindered one) is added to a toluene solution of the diol and triethylamine. Once the reaction is complete, the second diarylchlorophosphine is added. Triethylamine hydrochloride is filtered off and the solvent removed under reduced pressure to give the product.

The phosphinite-phosphites are synthesized as follows. Phosphorus trichloride is reacted with 1,1'-bi-2-naphthol to give the 1,1'-binaphthyl-2,2'-diyl phosphorochloridite. The chloridite is then reacted with either 1,1'-bi-2-naphthol or 2,2'-biphenol, followed by diphenylchlorophosphine. These reactions are all conducted stepwise in toluene with excess triethylamine present. The product is isolated by filtering off the triethylamine hydrochloride, then removing the solvent under reduced pressure.

The nonconjugated, acyclic, aliphatic, monoethylenically unsaturated starting materials useful in this invention include unsaturated organic compounds containing from 2 to approximately 30 carbon atoms. The 3-pentenenitriles and 4-pentenenitriles are especially preferred. As used herein, the term "pentenenitrile" is intended to be identical with "cyanobutene." Suitable unsaturated compounds include unsubstituted hydrocarbons as well as hydrocarbons substituted with groups which do not attack the catalyst, such as cyano. These unsaturated compounds include monoethylenically unsaturated compounds containing from 2 to 30 carbons such as ethylene, propylene, butene-1, pentene-2, hexene-2, etc.; nonconjugated diethylenically unsaturated compounds such as allene; and substituted compounds such as 3-pentenenitrile, 4-pentenenitrile, methyl pent-3-enoate; and ethylenically unsaturated compounds having perfluoroalkyl substituents such as, for example, $C_zF_{2z+1}$, where z is an integer of up to 20.

Other suitable substrates include 2-pentenenitrile and alkyl-2-pentenoate, where the alkyl group contains 1 to 12 carbon atoms.

Preferred substrates are nonconjugated linear alkenes, nonconjugated linear alkenenitriles, nonconjugated linear alkenoates, and perfluoroalkyl ethylenes. Most preferred substrates include 3- and 4-pentenenitrile, alkyl 3- and 4-pentenoates, where the alkyl group contains 1 to 12 carbon atoms, and $C_xF_{2x+1}CH=CH_2$ (where x is 1 to 12). The preferred products are terminal alkanenitriles, linear alkanedinitriles, linear alkane(nitrile)esters, and 3-(perfluoroalkyl) propionitrile. Most preferred products are adiponitrile, alkyl 5-cyanovalerate, and $C_xF_{2x+1}CH_2CH_2CN$ (where x is 1 to 12).

EXAMPLES

EXAMPLE 1

A. Synthesis of the compound depicted in Formula 16 above.

To a solution containing 1.60 g (5.59 mmol) of 1,1'-bi-2-naphthol and 2.0 mls (14.38 mmol) of triethylamine in 70 mls of toluene under a nitrogen atmosphere was added 2.50 g (11.33 mmol) of diphenylchlorophosphine. The mixture was allowed to stir at room temperature for an hour, then filtered to remove triethylamine hydrochloride. The filtrate and toluene washings of the Et$_3$N.HCl were combined and the solvent removed under reduced pressure to give 3.6 g of off-white solid. 31P NMR (CD$_2$Cl$_2$): 111.3 ppm, singlet.
B. Use of compound of Formula 16 above to hydrocyanate 3-pentenenitrile.

General hydrocyanation procedure: Reaction mixtures were heated in a thermostatically controlled oil bath. HCN vapor was delivered to the reaction flask as an HCN/N$_2$ gas mixture by bubbling dry N$_2$ gas through liquid HCN maintained at 0° C. in a wet ice bath. This provided a vapor stream which is roughly 35% HCN (vol/vol). The rate of HCN delivery was adjusted by varying the rate of N$_2$ flow. Sample analyses were done by gas chromatography using a DB-23 capillary column.

0.286 g of the compound from Part A and 40 mg of Ni(COD)$_2$ (COD is cyclooctadiene) were combined in 5 mls of tetrahydrofuran. After 5 minutes of stirring, the solvent was removed under reduced pressure and 5 ml of 3-pentenenitrile and 20 mg of ZnCl$_2$ were added. The mixture was treated with HCN vapor at a nitrogen flowrate of 12 cc/min and heated at 50, 60, 70, 80, 90, and 100° C. for 15 minutes at each temperature (except 30 minutes at 80° C.). After heating at 100° C., GC analysis indicated 36.8% adiponitrile, 12.0% methylglutaronitrile, and 1.2% ethylsuccinonitrile.

EXAMPLE 2

A. Synthesis of the compound depicted in Formula 17 above.

To a solution containing 1.04 g (5.59 mmol) of 2,2'-biphenol and 2.0 mls (14.38 mmol) of triethylamine in 50 mls of toluene under a nitrogen atmosphere was added 2.50 g (11.33 mmol) of diphenylchlorophosphine. The mixture was allowed to stir at room temperature for 30 minutes, then filtered to remove triethylamine hydrochloride. The filtrate and toluene washings of the Et$_3$N.HCl were combined and the solvent removed under reduced pressure to give a light brown solid. 31P NMR (CDCl$_3$): 112.2 ppm, singlet.
B. Use of compound of Formula 17 above to hydrocyanate 3-pentenenitrile.

0.233 g of the compound from Part A was combined with 1.0 ml of a ZnCl$_2$/3PN solution (0.50 g ZnCl$_2$ in 25 ml 3-pentenenitrile) and 4.0 ml of a Ni/3PN solution (1.11 g (o-TTP)$_2$Ni(ethylene) in 40 ml 3-pentenenitrile). The mixture was treated with HCN vapor at a nitrogen flowrate of 30 cc/min and heated at 70° C. for 1 hour. At this point, GC analysis indicated 11.0% adiponitrile, 3.2% methylglutaronitrile, and 0.3% ethylsuccinonitrile.

The compound from Part A was also employed in hydrocyanation where the molar ratio of ligand to nickel was 1:1.

Seventy-eight milligrams of the compound from Part A was added to 4 mls 3PN, followed by 0.040 g of Ni(COD)2 and 1.0 ml of a ZnCl$_2$/3PN solution (0.409 g ZnCl$_2$ in 20 mls 3PN). The mixture was heated to 70° C. and then treated with HCN vapor at a nitrogen flowrate of 30 cc/min for 1 hour. At this point, GC analysis indicated 26.2% adiponitrile, 7.9% methylglutaronitrile, and 0.04% ethylsuccinonitrile.

EXAMPLE 3

A. Synthesis of the compound depicted in Formula 18 above.

To a solution containing 0.56 g (3.0 mmol) of 2,2'-biphenol and 2.0 mls (14.38 mmol) of triethylamine in 50 mls of toluene under a nitrogen atmosphere was added a toluene solution of di(4-chlorophenyl)phosphinous chloride (1.74 g phosphine [6.0 mmol]in 20 mls toluene). The mixture was allowed to stir at room temperature for 2–3 hours, then filtered to remove triethylamine hydrochloride. The filtrate and toluene washings of the triethylamine hydrochloride were combined and the solvent removed under reduced pressure to give 1.98 g of a brown oil. 31P NMR (CDCl$_3$): 110.2 ppm, singlet. Also, a minor signal at 115.2 ppm.
B. Reaction of compound of Formula 18 above with Ni(COD)$_2$.

0.317 g of the compound from Part A and 0.126 g of Ni(COD)$_2$ (COD is cyclooctadiene) were combined in 15 mls of dry tetrahydrofuran under a nitrogen atmosphere. The mixture was allowed to stir at room temperature for 30 minutes, then the solvent was removed under reduced pressure. After further drying under vacuum, 0.370 g of black solid was obtained. 31P NMR (C$_6$D$_6$): 148.1 ppm, singlet. Also, some broad resonances centered at about 113 and 129 ppm.
C. Use of the compound from Part B above to hydrocyanate 3-pentenenitrile.

The compound from Part B, believed to be Ni(COD) (ligand) where ligand refers to the compound of Formula 18 above, was employed as the catalyst precursor in hydrocyanation without any extra ligand added.

One hundred twenty milligrams of the compound from Part B was added to 4.0 mls 3PN, followed by 1.0 ml of a $ZnCl_2$/3PN solution (0.409 g $ZnCl_2$ in 20 mls 3PN). The mixture was heated to 70° C. and then treated with HCN vapor at a nitrogen flowrate of 30 cc/min for one hour. At this point, GC analysis indicated 34.3% adiponitrile, 8.2% methylglutaronitrile, and 0.9% ethylsuccinonitrile.

Set forth in the Table 1 below are the results obtained when using bidentate phosphorus compounds in the process of the invention. It should be noted that the best results are considered to be those in which the total pentenenitrile (3-pentenenitrile+4-pentenenitrile, PN) conversion is relatively high (above about 20 percent), the percent distribution (selectivity) to adiponitrile (ADN) is high (above about 65 percent), and the percent conversion to 2-pentenenitrile (2PN) is low (below about 15 percent).

2-Pentenenitrile (2PN) is less reactive than 3- or 4-pentenenitrile for hydrocyanation to ADN, thus low 2PN yield is desired so as to minimize the required reaction time. It should further be noted that the lowest 2PN yields are obtained with phosphinites containing electron-withdrawing substituents.

The hydrocyanation procedure used to generate the results, shown in Table 1, is as follows: The compound to be tested is dissolved in 5 mls 3PN, then 0.14 mmol of either $Ni(COD)_2$ or $(oTTP)_2Ni(C_2H_4)$, followed by $ZnCl_2$, are added; the molar ratio of bidentate phosphorus compound to nickel is 3 to 1, and the molar ratio of nickel to zinc dichloride is 1:1. The reaction mixture is then heated to 70° C. and hydrogen cyanide is added continuously at a high flow rate (30 cc/min HCN/$N_2$) for one hour. Results are obtained by GC analysis of the reaction mixture.

In Table 1, the following definitions and abbreviations are used: Total 3-pentenenitrile and 4-pentenenitrile conversion to dinitriles is abbreviated as total PN conv to DN's. ADN distribution is calculated as:

$$(\% \, ADN \text{ distribution}) = \frac{100([ADN])}{([ADN] + [MGN] + [ESN])}$$

$$\% \, 2PN \text{ yield is calc. as: } \frac{100([2PN]_{Final} - [2PN]_{Initial})}{3PN + 4PN \text{ Conversion}}$$

Negative values for % 2PN yields should be interpreted as zero.

TABLE 1

| COMPOUND | TOTAL PN CONV TO DN'S | % ADN DIST | % 2 PN YIELD |
|---|---|---|---|
| Formula 2 | 53.6 | 73.9 | 1.56 |
| Formula 9 | 33.5 | 75.7 | 12.54 |
| Formula 14 | 19.7 | 67.1 | −1.33 |
| Formula 1 | 90.6 | 74.0 | 1.54 |
| Formula 15 | 81.9 | 75.5 | 1.57 |
| Formula 11 | 53.2 | 74.7 | 3.92 |
| Formula 6 | 60.7 | 76.3 | 12.88 |
| Formula 5 | 22.1 | 73.3 | 19.22 |
| Formula 17 | 14.1 | 75.7 | 23.3 |
| Formula 13 | 18.2 | 80.9 | −4.06 |
| Formula 16 | 59.0 | 73.5 | 21.95 |

TABLE 2

3PN Hydrocyanation results for two compounds with various Lewis Acid Promoters.
Reaction Conditions: 70° C., 30 cc/min HCN/$N_2$. 0.14 mmol $Ni(COD)_2$ as catalyst precursor. On molar basis, ratios were 1:1:3 Ni:Lewis Acid:ligand in 5 mls 3PN. Results given for 60 minute sample.

| | COMPOUND OF FORMULA 16 RESULTS | | COMPOUND OF FORMULA 1 RESULTS | |
|---|---|---|---|---|
| LEWIS ACID | % ADN DIST | % TOTAL PN CONV TO DN'S | % ADN DIST | % TOTAL PN CONV TO DN'S |
| $ZnC_{12}$ | 74.2 | 50.9 | 74.7 | 80.5 |
| $MnCl_2$ | 74.5 | 50.0 | 78.5 | 67.2 |
| $FeCl_2$ | 74.0 | 56.1 | 75.3 | 74.5 |
| $LaCl_3$ | 58.8* | 1.7 | Expt Not Run | Expt Not Run |
| $YCl_3$ | 65.3* | 4.0 | 82.6 | 4.8 |
| $BPh_3$ | 84.8* | 7.6 | 97.2 | 16.7 |
| $AlCl_2(C_8H_{17})$ | 80.7 | 60.0 | 72.9 | 41.6 |
| Repeat | 81.3 | 57.4 | Expt Not Run | Expt Not Run |
| $Ph_3Sn(Ph_3BCN)$ | 97.4 | 67.7 | 97.5 | 44.6 |
| $SmCl_3$ | 68.0* | 4.4 | Expt Not Run | Expt Not Run |
| $Er(OTf)_3$ | 89.2 | 15.9 | Expt Not Run | Expt Not Run |
| $Ph_3Sn(DBS)$ | 98.2 | 20.7 | 97.3 | 12.7 |

In Table 2, Ph is $C_6H_5$. OTf is $CF_3SO_3$. DBS is $CH_3(CH_2)_{11}C_6H_4SO_3$. PN is pentenenitrile. DN is dinitrile. ADN is adiponitrile.

In the table, the % ADN distributions labelled with * have been corrected for the methylglutaronitrile (MGN) derived from hydrocyanation of 2-methyl-3-butenenitrile (2M3). 2M3 was initially present as an impurity in the 3PN used for these experiments. The corrected distribution was calculated as follows:

$$\% \, ADN \text{ distribution} = \frac{100([ADN])}{([ADN] + [MGN] + [ESN] - [2M3])}$$

where [2M3] refers to the amount of 2-methyl-3-butenenitrile found in the 3PN before hydrocyanation was begun. ESN refers to ethylsuccinonitrile.

What is claimed is:

1. A hydrocyanation process which comprises: reacting a compound selected from the class consisting of 2-pentenenitrile, 3-pentenenitrile, 4-pentenenitrile, alkyl-3-pentenoate, alkyl-4-pentenoate, or $C_zF_{2z+1}CH=CH_2$, wherein z is 1 to 12 with hydrogen cyanide in the presence of a Lewis Acid promoter and a catalyst comprising a zero-valent nickel compound and a compound selected from the group consisting of bidentate phosphorous compounds having the formulae:

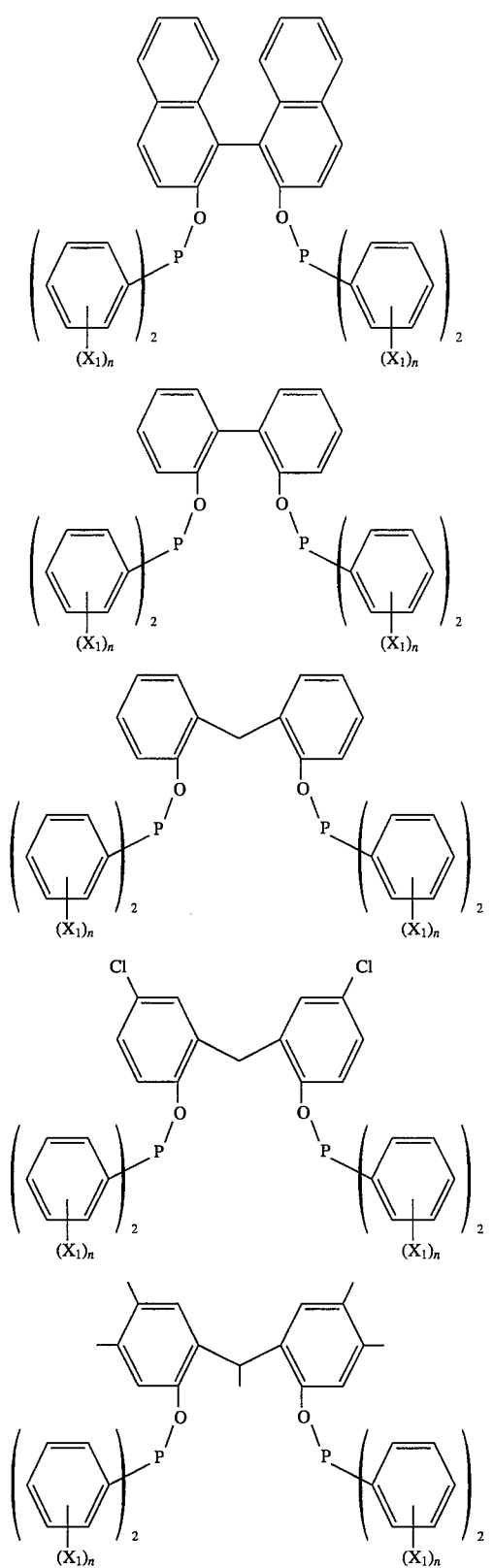
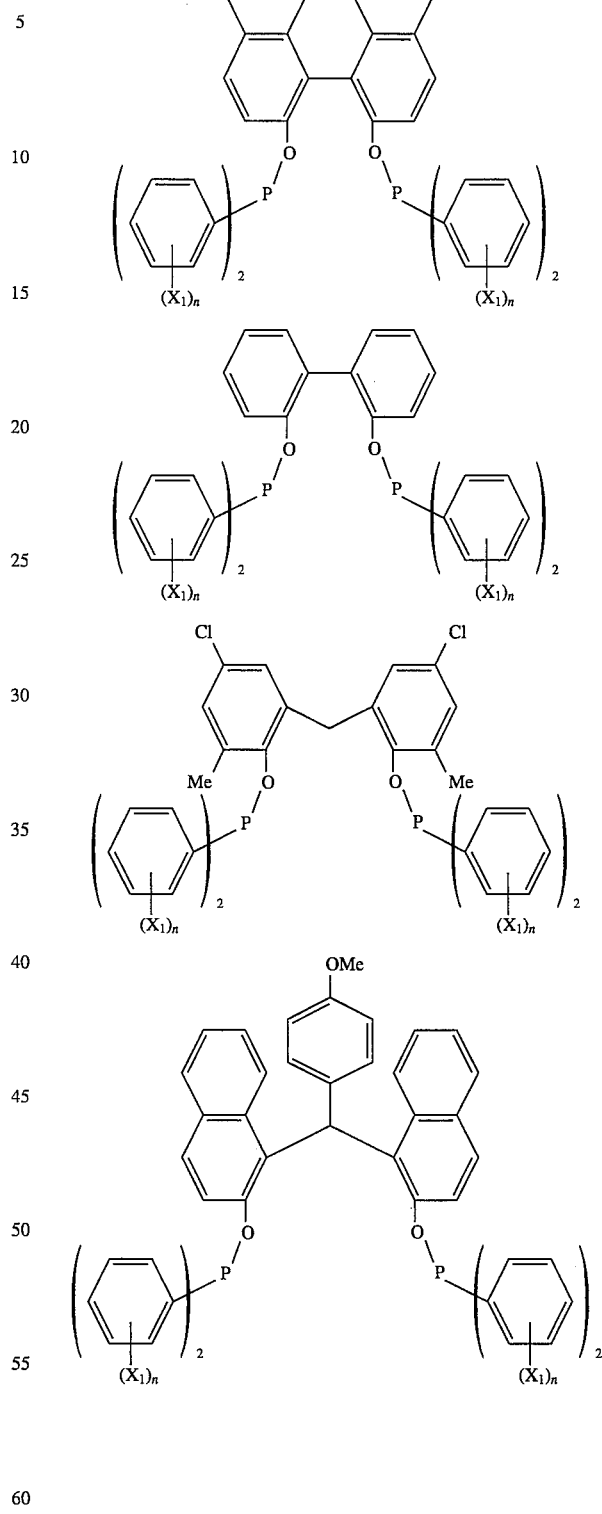

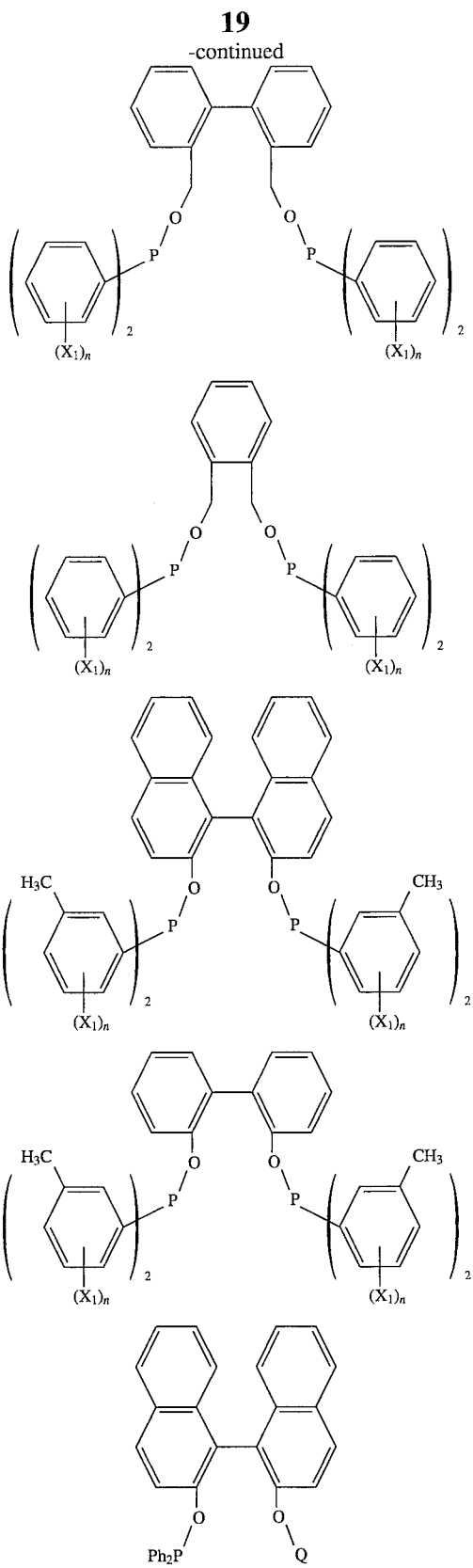

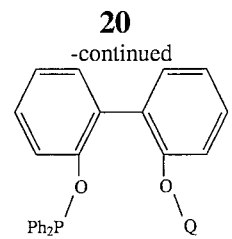

where $X_1$ is meta —Cl, para —Cl, meta —$CF_3$, para —$CF_3$, meta —F, para —F, meta —CN, para —CN, meta —$CH_3$ or para —$CH_3$; $X_2$ is methyl or alkoxy having 1 to 3 carbon atoms; n is zero, 1 or 2; Q is where Q is

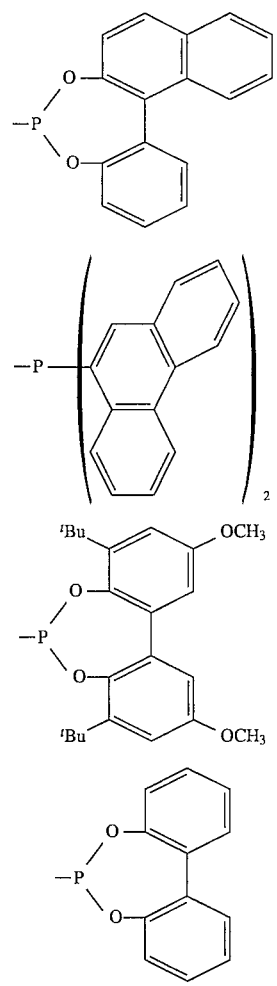

where the mole ratio compound to be hydrocyanated to catalyst is about 10:1 to 2000:1; the mole ratio of Lewis Acid to nickel is about 1 to 16 to 50 to 1; and the mole ratio of bidentate phosphorous compound to nickel is about 0,5:1 to 20:1, at a temperature of −25° to 200° C. and at a pressure of 0.05 to 10 atmospheres, and the hydrogen cyanide adds to the double bond of the reacting compound in primarily an anti-Markownikoff manner.

2. The process of claim 1 in which the bidentate phosphorous compound is selected from the group consisting of compounds having the formulae 1 through 21 in the specification.

3. The process of claim 2 in which the bidentate phosphorous compound is selected from the group consisting of compounds having the formulae 1, 2, 4, 6, 7, 8, 9, 10, 11, 13, 14, 15, 18 in the specification.

4. A process of claim 1 wherein the Lewis Acid is selected from the group consisting of inorganic or organometallic compounds in which the cation is selected from scandium, titanium, vanadium, chromium, manganese, iron, cobalt, copper, zinc, boron, aluminum, yttrium, zirconium, niobium, molybdenum, cadmium, rhenium, and tin.

5. The process of claim 1 wherein the Lewis Acid is selected from the group consisting of $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2(THF)_2$, $TiCl_4(THF)_2$, $TiCl_4$, $TiCl_3$, $ClTi(O-iPr)_3$, $MnCl_2$, $ScCl_3$, $AlCl_3$, $(C_8H_{17})AlCl_2$, $(iso-C_4H_9)_2AlCl$, $(phenyl)_2AlCl$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $TaCl_5$, $B(C_6H_5)_3$, and $(C_6H_5)_3SnX$, where $X=CF_3SO_3$, $CH_3C_6H_4SO_3$, $CH_3(CH_2)_{11}C_6H_4SO_3$, or $(C_6H_5)_3BCN$.

* * * * *